United States Patent
Gupta et al.

[11] Patent Number: 5,888,122
[45] Date of Patent: Mar. 30, 1999

[54] METHOD FOR MANUFACTURING AN INTRAOCULAR LENS

[75] Inventors: Amitava Gupta; José Ulloa, both of Roanoke, Va.

[73] Assignee: Prism Ophthalmics, L.L.C., Roanoke, Va.

[21] Appl. No.: 834,831

[22] Filed: Apr. 10, 1997

[51] Int. Cl.⁶ .............................. B24B 7/22; B24B 1/00; A61F 2/16

[52] U.S. Cl. .............................. 451/42; 451/43; 351/177; 623/6

[58] Field of Search ............................... 351/160 R, 161, 351/175, 177; 451/42, 43; 623/6

[56] References Cited

U.S. PATENT DOCUMENTS

| | | | |
|---|---|---|---|
| 3,245,745 | 4/1966 | Hancock | 351/167 |
| 4,504,982 | 3/1985 | Burk . | |
| 4,551,949 | 11/1985 | Akhavi et al. | 451/32 |
| 4,581,031 | 4/1986 | Koziol et al. | 623/6 |
| 4,641,934 | 2/1987 | Freeman | 351/159 |
| 4,648,878 | 3/1987 | Kelman | 623/6 |
| 4,685,921 | 8/1987 | Peyman | 623/6 |
| 4,685,922 | 8/1987 | Peyman | 623/6 |
| 4,731,078 | 3/1988 | Stoy et al. | 623/6 |
| 4,749,530 | 6/1988 | Kunzler | 451/42 X |
| 4,779,972 | 10/1988 | Gottlieb | 351/177 |
| 4,786,657 | 11/1988 | Hammar et al. | 522/90 |
| 4,828,558 | 5/1989 | Kelman | 623/6 |
| 4,856,234 | 8/1989 | Goins | 451/32 X |
| 4,923,296 | 5/1990 | Erickson | 351/161 |
| 4,932,970 | 6/1990 | Portney | 623/6 |
| 4,957,506 | 9/1990 | Mercier . | |
| 5,002,383 | 3/1991 | Sisler | 351/175 |
| 5,089,023 | 2/1992 | Swanson | 623/6 |
| 5,096,285 | 3/1992 | Silberman | 351/161 |
| 5,151,723 | 9/1992 | Tajiri | 351/161 |
| 5,171,267 | 12/1992 | Ratner et al. | 623/6 |
| 5,195,407 | 3/1993 | Takano et al. | 451/42 X |
| 5,322,649 | 6/1994 | Rheinish et al. | 83/50 X |
| 5,443,507 | 8/1995 | Jacobi | 623/6 |
| 5,549,668 | 8/1996 | O'Donnell, Jr. | 623/6 |
| 5,571,558 | 11/1996 | Nguyen et al. | 451/32 X |
| 5,683,457 | 11/1997 | Gupta et al. | 623/6 |

*Primary Examiner*—Timothy V. Eley
*Attorney, Agent, or Firm*—Finnegan, Henderson, Farabow, Garrett, & Dunner, L.L.P.

[57] ABSTRACT

A method of manufacturing an intraocular lens for restoring visual function to an eye. The lens includes a convex lens optic for receiving and focusing light rays, a prismatic wedge adjacent to the convex lens optic for receiving and directing light rays to a functional portion of a retina of the eye, and structure for fixing the lens optic and the prismatic wedge in the eye so that the lens optic is angularly oriented with respect to an optic axis of the eye and is posterior to the prismatic wedge. The lens optic includes an aspheric surface having a geometry determined according to a specific formula.

21 Claims, 8 Drawing Sheets

METHOD FOR MANUFACTURING AN INTRAOCULAR LENS

BACKGROUND OF THE INVENTION

1. Field of the Invention

The present invention relates to prismatic intraocular lenses for restoring vision in patients with macular degeneration. More particularly, the present invention relates to prismatic intraocular lenses having aspheric surface geometry and related methods of their manufacture.

2. Description of the Related Art

As shown in FIG. 1, a normal eye 10 includes a cornea 12, an aqueous solution called the aqueous humor 14 behind cornea 12, an iris 16, a natural lens 18, ciliary sulcus 20, retina 22, macula 24 at the center of the retina, and fovea 26 at the center of macula 24. The cornea 12 and lens 18 cause an image 30 to form at fovea 26. Fovea 26 is a circular zone approximately 0.2–0.5 mm$^2$ in area. The image 30 formed at fovea 26 corresponds to a locus of fixation for providing acute vision. This locus of fixation helps to coordinate voluntary and involuntary head and eye movements required for daily activities, such as reading, driving, and dressing. Peripheral images are located around this locus of fixation.

A common cause of blindness in adults is macular degeneration. This retinal disease involves damage to the fovea so that the fovea is unable to process images. The damage spreads over time into the macula and beyond, causing a blind spot at the center of a patient's visual field. The patient is thus unable to read, drive, or perform other tasks that require the brain to reference the locus of fixation.

In most patients, even in those with advanced macular degeneration, the macula is not completely damaged, but retains healthy areas. However, the loss of the locus of fixation caused by the central blind zone leads to severe visual impairment and often to legal blindness, defined as visual acuity of 20/200 or less. The number of patients diagnosed with such severe visual impairment in the United States alone exceeds 2 million.

Intraocular lens implants have been devised to replace the natural lens of the eye and restore sight to damaged or diseased eyes. The intraocular implant directs image forming light rays to a healthy portion of the macula. One such implant is an intraocular lens which forms part of a telescopic optic. Such an implant includes a convex lens forming the eye piece of a Galelian optic. The objective lens of the telescope is provided by another plus lens which may be provided in the form of a contact lens or a spectacle lens.

Compound intraocular lenses that combine different optical elements also have been proposed. In such proposals, a diffractive/refractive lens implant includes a diffractive lens profile covering about half the effective lens area. Such a configuration allows about half of the incident light from distant objects and half of the incident light from near objects to enter the eye. Such a compound optic provides an ability to form on the retina a focused image of both distant objects and near objects.

Although both images are formed on the fovea, the brightness of the image in each case is reduced by about 50%, or the ratio of the light intensity assigned to each image. In certain cases, such a lens can be used to treat macular degeneration by providing sufficient image magnification so as to project the image over a retinal area more than that damaged by macular degeneration. Such an approach, however, does not shift the image to healthy portions of the retina.

Similar multifocal intraocular lenses incorporating two refractive zones also have been disclosed. For example, the use of a pair of bifocal intraocular lenses has been disclosed in which each of the pair of bifocal intraocular lenses incorporates a refractive element and a diffractive element. One of the lenses provides greater image intensity for the image of near objects, while the other lens provides greater image intensity for the image of distant objects. This approach has the advantage that the incident light can be apportioned or split between the two images in a continuous manner between the two lenses. The disadvantage is that the image is processed by two optical elements, each of which introduces its own aberrations and loss of image contrast so that the performance of the compound lens can be worse than either a diffractive or refractive lens.

Intraocular lenses incorporating a single refractive element also have been devised to shift the image from a damaged portion of the retina to a healthy area. One such example is a prismatic intraocular lens that includes a convex spherical lens portion for focusing light rays and a prism posterior to the convex lens for deflecting light away from the diseased center of the retina to a functional point. This amount of deflection provided by the prism depends upon the prism vector, i.e. the prism wedge angle and the orientation of the prism with respect to the nasal-temporal axis of the retina.

Such prismatic intraocular lenses restore the central field vision to a patient. Prior prismatic intraocular implants, however, do not provide any means for correcting optical aberrations such as astigmatism, coma, and spherical aberration introduced by the prismatic portion. Consequently, the quality of the image delivered by prior prismatic intraocular lenses is poor, and may not provide significant benefit to patients implanted with such devices. Thus, there is a continuing need to improve the image quality provided by such lenses.

SUMMARY OF THE INVENTION

Accordingly, an object of this invention is to provide an improved prismatic intraocular lens that provides superior image quality, and a related method of manufacturing such an intraocular lens.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises an intraocular lens for restoring visual function to an eye. The lens includes a convex lens optic for receiving and focusing light rays, a prismatic wedge adjacent to the convex lens optic for receiving and directing light rays to a functional portion of a retina of the eye, and structure for fixing the lens optic and the prismatic wedge in the eye so that the lens optic is angularly oriented with respect to an optic axis of the eye.

The lens optic of the intraocular lens includes an aspheric surface determined according to the following formula:

$$Z(h) = ch^2/(1 + \{1 - (1+k)\, c^2 h^2\}^{1/2})$$

where $Z(h)$=position of the aspheric surface on a z axis as a function of a radial distance h of the aspheric surface from the center of an optical blank, h=radial distance of the aspheric surface from the center of the optical blank, c=average aspheric curvature, and k=conic constant.

According to another aspect, the invention comprises a method for manufacturing an intraocular lens for restoring visual function to an eye. The intraocular lens includes a convex lens optic for receiving and focusing light rays, a prismatic wedge adjacent to the convex lens optic for receiving and directing light rays to a functional portion of a retina of the eye, and means for fixing the lens optic and the prismatic wedge in the eye. The method includes the steps of providing an optical blank, forming a conic section having an aspheric surface and a flange portion from the optical blank, forming the prismatic wedge and lens optic from the conic section, and forming the fixation means from the flange portion.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate an embodiment of the invention and together with the description, serve to explain the principles of the invention. In the drawings.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

The present invention is directed to a prismatic intraocular lens and a related method of manufacture. The prismatic intraocular lens is for replacing the natural lens of an eye that suffers from macular degeneration or other macular diseases. The prismatic intraocular lens according to the present invention includes a convex lens optic for receiving and focusing light rays and a prismatic wedge adjacent to the convex lens optic for receiving and directing light rays to a functional portion of a retina of the eye. The prismatic wedge deflects the position of the image from a blind spot at the center of the eye, possibly a macular hole, to a functional area in the retina. The lens optic and prismatic wedge are positioned and fixed in the eye, preferably through the use of a pair of haptics, so that the lens optic is angularly oriented with respect to the optic axis of the eye and so that the prismatic wedge is anterior to the lens optic. The surface of the convex lens optic has an aspheric geometry. The geometry used for a particular application is determined according to a formula to be described herein.

The aspheric geometry and the relative positioning of the lens optic and prismatic wedge in the eye according to this invention improve the total modulation transfer function delivered by the intraocular lens. In other words, the inventive intraocular lens and its positioning within the eye improve overall image quality, i.e., the contrast versus resolution performance. This has been determined through computer modeling, also to be described herein.

A prismatic intraocular lens according to an embodiment of the present invention is of a single, one-piece construction. The lens is manufactured from an optical blank of suitable material that is machined in separate steps to form an aspheric surface, the prismatic wedge, and the structure for fixing the intraocular lens in the eye. The details; of these steps are provided herein.

Figure 1:
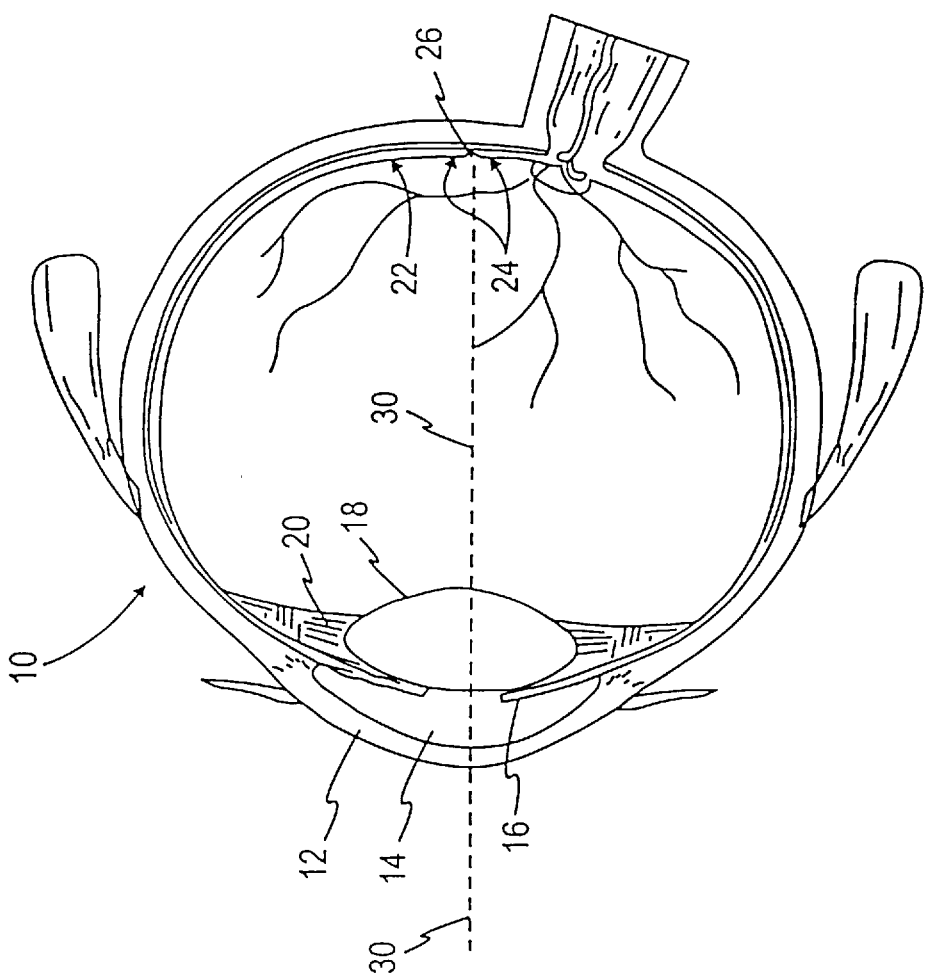
FIG. 1 is a side elevation sectional view of a normal human eye having a natural lens.
Figure 2:
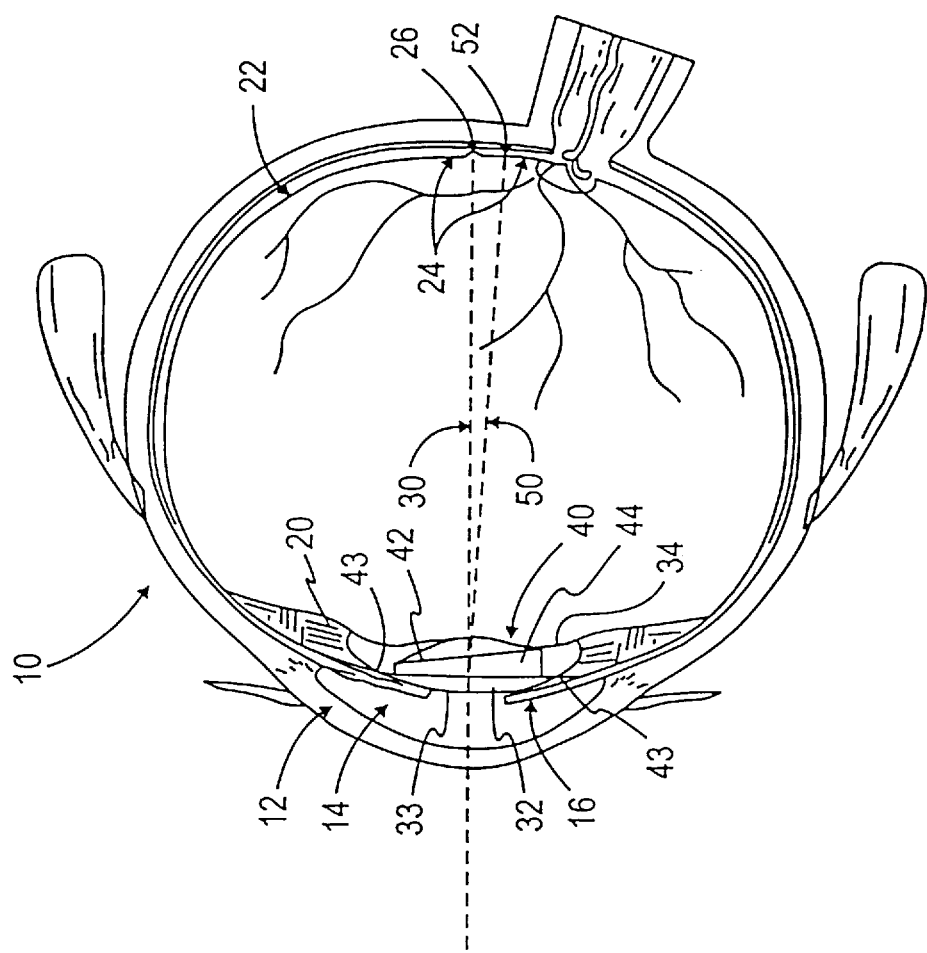
FIG. 2 is a side elevation sectional view of an eye incorporating a prismatic intraocular lens according to the present invention.
Figure 4:
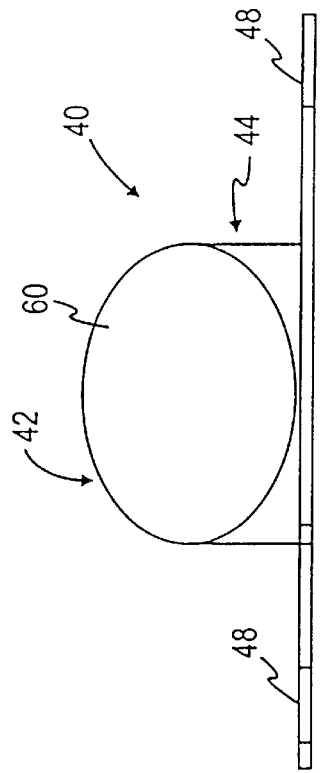
FIG. 4 is a side elevation view of the lens shown in FIG. 3.
Figure 6:
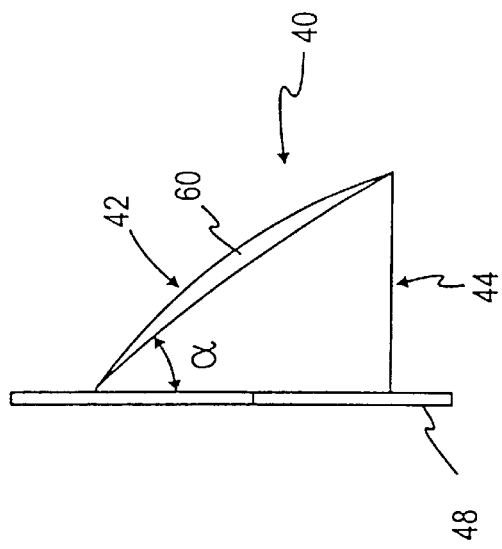
FIG. 6 is another side elevation view of the lens shown in FIG. 3.
Figure 3:
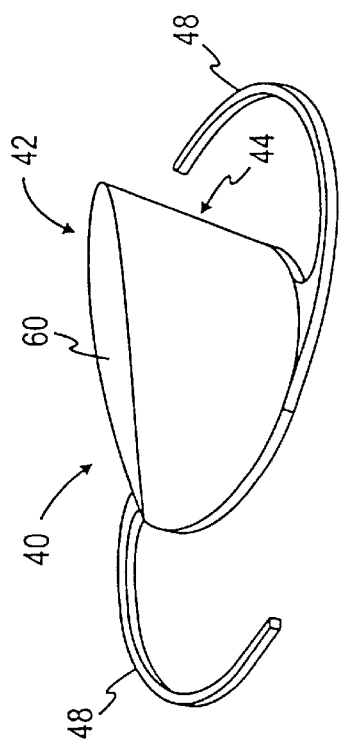
FIG. 3 is a perspective view of a prismatic intraocular lens according to the present invention.
Figure 5:
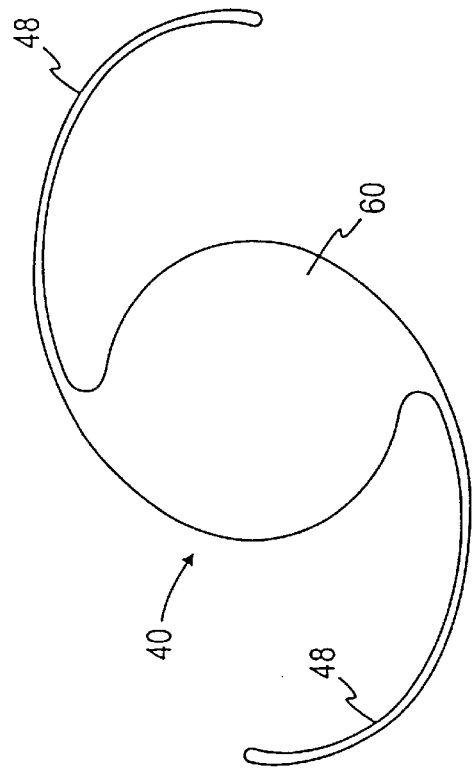
FIG. 5 is a plan view of the lens shown in FIG. 3.

As shown in FIGS. 3 to 6, a prismatic intraocular lens 40 according to an embodiment of the present invention includes two major optical components, a convex lens portion 42 for focusing the image and a prism wedge 44 adjacent to lens portion 42 for redirecting the image to a functional portion of the retina. As shown in FIG. 2, image 30 that forms at fovea 26 in a normal eye will be redirected to image 50 for shifting the image location to a healthy retinal area 52. The magnitude of an angle α of prism wedge 44 (FIG. 6) and the orientation of prism wedge 44 with respect to the nasal-temporal axis of the retina, as shown in FIG. 2, determines the area 52 of the retina to which the image is shifted.

With reference once again to FIGS. 3 to 6, convex lens portion 42 includes a surface 60 preferably having an aspheric geometry. Aspheric optics improve the quality of the retinal image by minimizing spherical aberration. Spherical aberration is caused by the failure of light rays incident on various parts of the optic to come to a single focus. The resulting image is therefore blurry. The geometry of lens surface 60 is aspheric in shape to correct for spherical aberration and to restore image contrast at the focal point. As mentioned, the specific aspheric geometry to be used for a particular application is determined according to a formula to be described below.

The prismatic intraocular lens according to the present invention must be positioned and firmly supported and fixed within the eye to lessen its susceptibility to rotational displacement. Unwanted rotational displacement will potentially move the deflected image from a healthy retinal area to a dysfunctional area.

In the preferred embodiment, haptics 48, shown in FIGS. 3 to 6, are used to support and fix lens portion 42 and prism wedge 44 in the eye. The compressive force exerted by haptics 48 on lens portion 42 and prism wedge 44 prevents rotational or tilting displacement and ensures stability. Preferably, each haptic 48 is integrally formed with lens portion 42 and prism wedge 44 and from the same material to form a single piece construction. Each haptic 48 preferably radiates out from prism wedge 44 in the form of a modified C.

In the preferred embodiment, prismatic intraocular lens 40 is placed in the capsular sac 32 of the eye after removal of the patient's natural lens. It is most preferred that the piano surface of prismatic intraocular lens 40, i.e. the surface adjacent prism wedge 44, be placed anterior, and the convex surface of lens portion 42 be placed posterior, as shown in FIG. 2. According to this embodiment, the piano surface is placed next to the anterior capsule 33, and the convex surface of lens portion 42 is in intimate contact with the posterior capsule 34. The contact between the lens portion 42 and the posterior capsule helps to eliminate any space that may fill with stagnant aqueous humor (eye fluid) and thereby reduce the risk of bacterial growth and toxin production in the eye. The anterior placement of the piano surface of prismatic intraocular lens 40, prism wedge 44, and haptics 48 lessens forward movement of lens 40. Such movement could cause contact with the iris and inflammation of the iris as the iris opens and closes throughout the day. Also, it is preferred that lens portion 44 is angularly oriented with respect to the nasal-temporal axis of the eye, as also shown in FIG. 2.

It is to be understood that other positions within the eye are within the scope of this invention. For example, the intraocular lens may be placed in capsular sac 32 with lens portion 42 anterior to prism wedge 44 and the piano surface of prismatic intraocular lens 40. As another alternative, the prismatic intraocular lens may be placed in the ciliary sulcus, or the anterior chamber of the eye, and secured therein by fixing means such as haptics 48.

A preferred material for intraocular lens 40, especially for 1–2 mm image shifts, is polymethyl methacrylate (PMMA). PMMA has a refractive index of 1.498. For shifts greater than 2.0 mm, a material of higher refractive index should be used. An image shift of 3.0 mm or greater is rarely encountered since visual acuity drops steeply with distance radially away from the fovea to as much as 20/200 or lower.

Preferably, a prismatic intraocular lens according to this invention is integrally manufactured to form a single-piece, integral construction. In other words, the convex lens portion, prismatic wedge, and haptics are preferably manufactured by molding or machining a unitary optical blank made of a machinable material, such as a thermoplastic like PMMA. A suitable size blank is approximately 3–10 mm thick and 15–30mm in diameter.

A preferred method for manufacturing a prismatic intraocular lens according to an embodiment of the present invention includes three main steps, a first step for forming the aspheric surface, a second step for forming the prismatic wedge, and a third step for forming the haptics.

Prior to manufacturing a prismatic intraocular lens according to this invention, the power of the convex lens portion and the prism wedge angle must be determined by measuring certain parameters and characteristics of the patient's eye using standard techniques well known in the optical art. The power of the lens portion depends on the length of the optic axis of the eye and the spherical power of the patient's cornea. The optic axis of the eye is determined by ultrasonic imaging of the eye, a standard procedure preceding the removal of the crystalline lens of the eye and implantation of an intraocular lens. Corneal power is determined by measuring corneal curvature and corneal thickness, again through standard ultrasonic image scanning techniques. Based on the length of the optical axis and corneal power, the power of the convex lens portion is determined using standard optical formulas.

A method of determining the necessary prism wedge angle is described in commonly assigned U.S. patent application Ser. No. 08/647,228 filed May 9, 1996 and entitled "Prismatic Intraocular Lenses and Related Method of Using Such Lenses To Restore Vision in Patients With Central Field Loss." The disclosure of that application is incorporated by reference. That disclosure teaches that, in order to accurately determine the prism wedge angle, a patient with visual impairment due to central field loss is subjected to a series of diagnostic tests to determine the position of healthy, functional areas of the retina. Precise measurements are made to determine the distance from the fovea to the desired points of image fixation in each eye. The magnitude of the prism wedge angle is then calculated according to the following formula:

$$\alpha = 360 d/2\pi a(n_1 - n_2) \qquad \text{Equation (1)}$$

where α=magnitude of prism wedge angle in degrees;
  d=the distance from the fovea to the desired healthy point of image fixation on the retina;
  $n_1$=the refractive index of the prismatic intraocular lens material;
  $n_2$=the refractive index of the aqueous solution in the aqueous humor, typically about 1.334; and
  a=the distance from the fovea to the posterior plane of the intraocular lens. The distances d and a are determined from the patient's diagnostic tests.

Once the power of the lens and the prism wedge angle have been determined, the prismatic intraocular lens is manufactured. The first step in the manufacturing process forms an aspheric surface from an optical blank. A portion of the aspheric surface will define lens surface 60, as will be described later.

Figure 10:
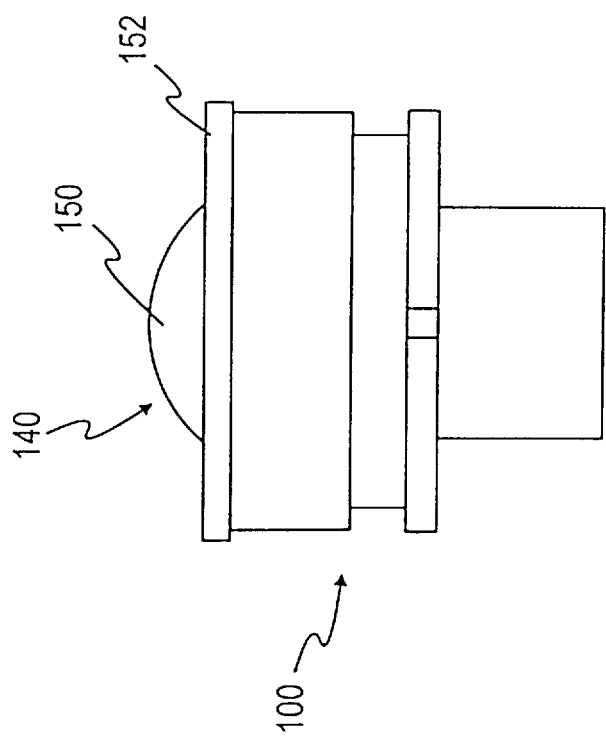
FIG. 10 is a side elevation view of the partially constructed lens and arbor of FIG. 9.
Figure 9:
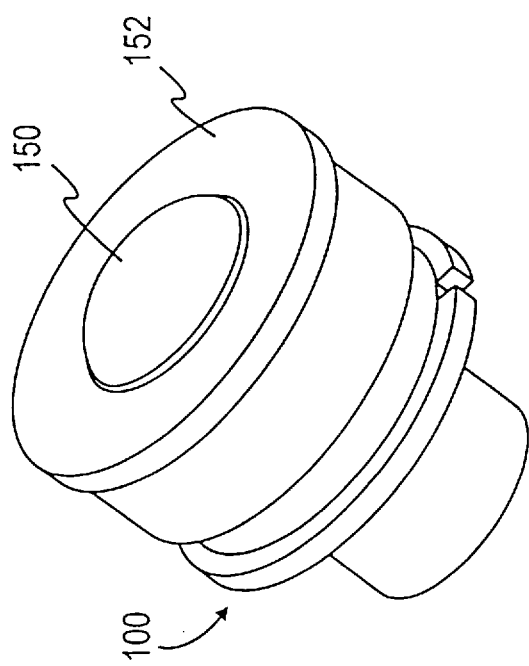
FIG. 9 is a perspective view of a partially constructed prismatic intraocular lens, according to the present invention, mounted onto an arbor for use in a manufacturing process according to the present invention.

In the first step, the blank is mounted on a standard plastic fixture or spindle called an arbor. Wax or any suitable method may be used to mount the blank onto the arbor. The blank is then machined on a standard lathe to form a conic section having an aspheric surface and a flange portion, or flat skirt, around the section. FIGS. 9 and 10 show an embodiment of an arbor 100 for use in this first step of the manufacturing process and a machined part mounted thereon. The part includes a flat skirt 152 and a conic section 140 having an aspheric surface 150.

The lathe is programmed with the following formula to machine aspheric surface 150 of conic section 140:

$$Z(h) = ch^2/(1 + \{1-(1+k)c^2h^2\}^{1/2}) \qquad \text{Equation (2)}$$

where Z(h)=position of aspheric surface 150 on the z axis as a function of the radial distance h of aspheric surface 150 from the center of the optical blank;

h=radial distance of aspheric surface 150 from the center of the optical blank;

c=average aspheric curvature=1/R, where R=curvature; and k=conic constant (a measure of the disfigure from a comparable circle).

Figure 7:
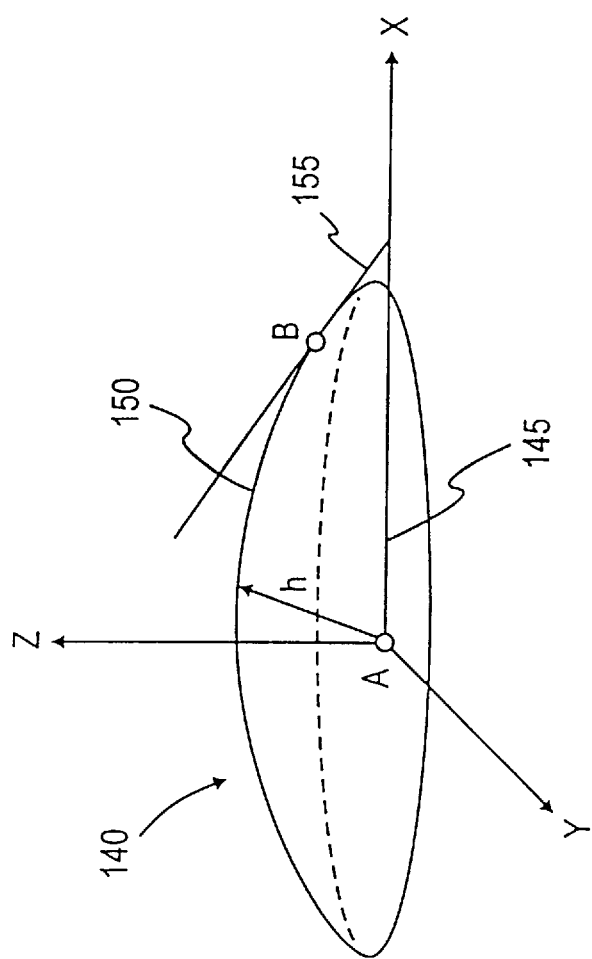
FIG. 7 is a perspective view of a conic section having as aspheric surface formed in the manufacturing process of a prismatic intraocular lens according to the present invention.

Each of these variables will now be explained. FIG. 7 shows a conic section 140 having an aspheric surface 150 formed by Equation (2) above. Conic section 140 has its flat surface 145 sitting on an x-y plane and centered at point A. The remaining curved surface of conic section 140 is aspheric surface 150. A z-axis is perpendicular to flat surface 145 and runs through center point A. Z(h) represents the position of aspheric surface 150 on the z axis as a function of the radial distance h of aspheric surface 150 from the center of the optical blank.

For a particular application, the variable c is determined according to the power of the convex lens portion, as determined above. The curvature R of the lens portion is, determined from the power of the lens portion by using standard optical formulas known in the art. Variable c is the inverse of R.

Also for a particular application, the variable k is determined according to computer software. The software performs many simulations of the passage of light rays through an intraocular lens having a convex lens of the required power and a prism wedge of the required wedge angle. The value of k is varied (the disfigure of the lens from a comparable circle is varied) and the software assesses the resulting image. The value of k that produces the highest image contrast is the optimum value of k used in Equation (2) above. The spherical aberration and astigmatism are minimized in order to obtain this optimum value. Suitable computer software for performing the above-described simulations and determining an optimum value of k is commercially available. One suitable software is sold under the name Code V.

As an example, according to a computer simulation, for an intraocular lens implant having a power of 20 diopters with a 20° wedge angle, c=1/(7.7765 mm) and, according to the Code 5 software, k=0.302406. The lathe is programmed with Equation (2) and the values of c and k. Equation (2) controls the lathe to accurately cut the optical blank and form aspheric surface 150 of conic section 140 and flat skirt 152. The aspheric geometry of surface 150 is determined by plugging the values of c and k into Equation (2). For each coordinate h, a value of Z(h) is determined that defines a point on surface 150. Suitable computer programs used to control the lathe are well known and commercially available. For example, a suitable commercially available computer program is P-MAC™ manufactured by Delta-Tau Corporation.

Alternatively, the lathe may be programmed with a table of coordinates of points obtained from Equation (2) that describe the location in space of the lathe tool point. Such a table of coordinates is typically referred to as a sag height table because it describes the sagittal height of points on the surface of the optic lens after machining.

Figure 12:
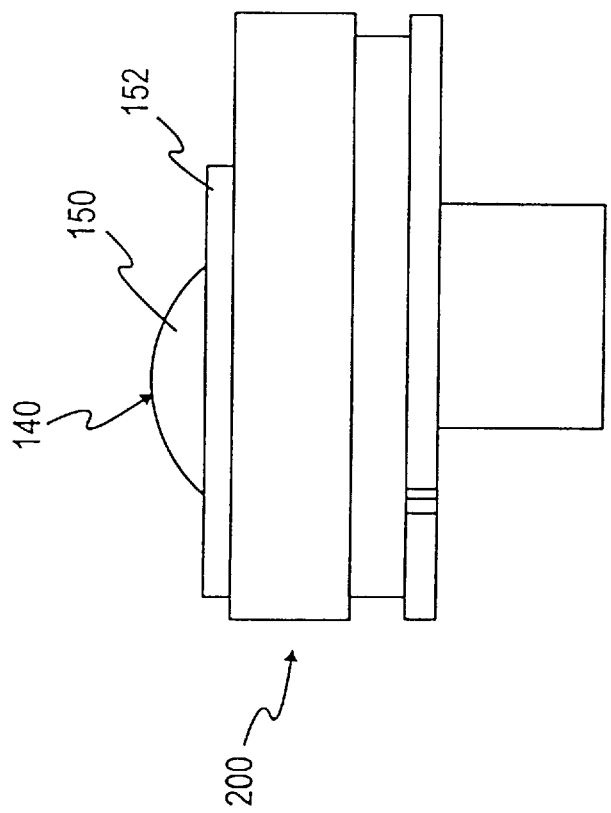
FIG. 12 is a side elevation view of the partially constructed lens and arbor of FIG. 11.
Figure 11:
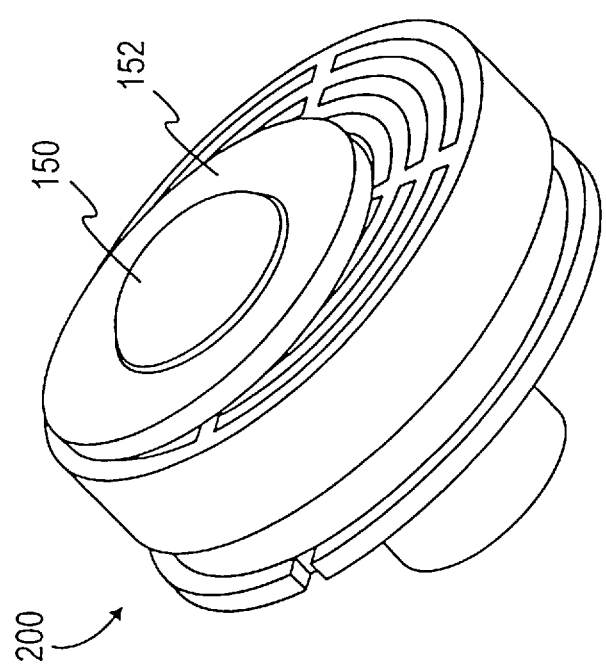
FIG. 11 is a perspective view of a partially constructed prismatic intraocular lens, according to the present invention, eccentrically mounted onto a second arbor for use in a manufacturing process according to the present invention.
Figure 14:
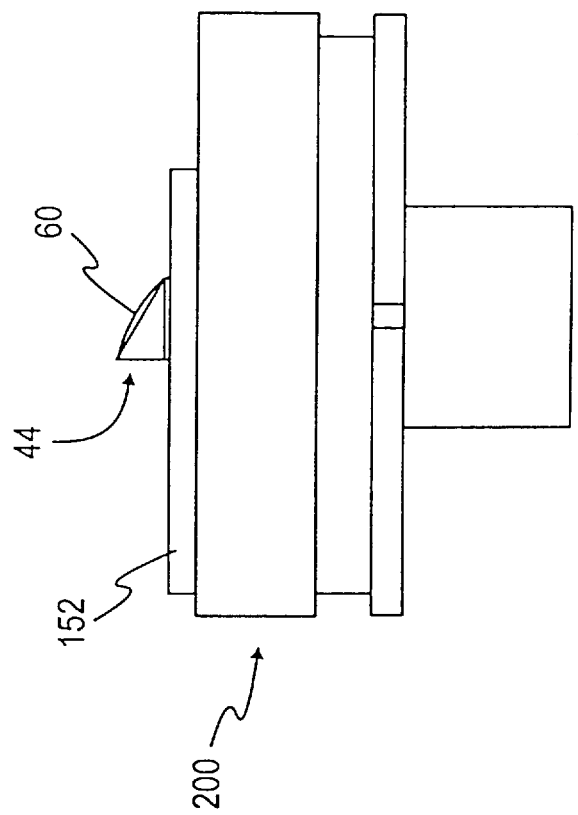
FIG. 14 is a side elevation view of the partially constructed lens and arbor of FIG. 13.
Figure 13:
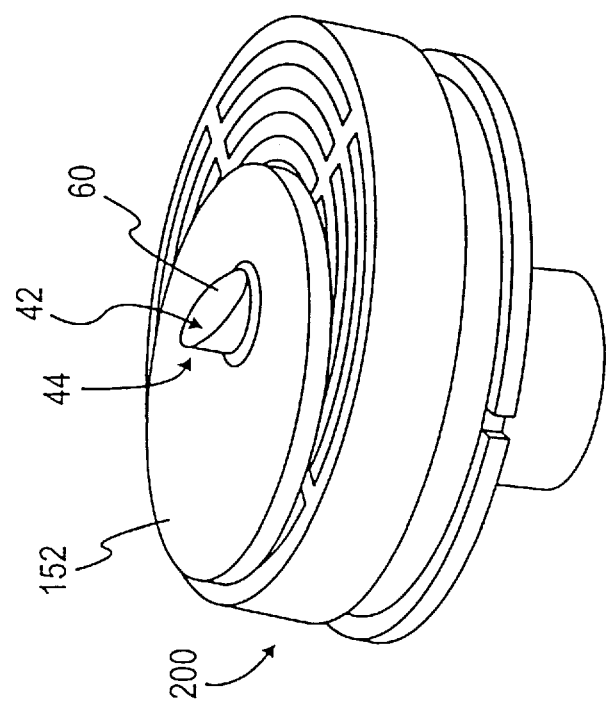
FIG. 13 is a perspective view of a partially constructed prismatic intraocular lens, according to the present invention, eccentrically mounted onto the second arbor for use in a manufacturing process according to the present invention.

Once aspheric surface 150 and flat skirt 152 are formed, the resulting machined part is dismounted from arbor 100 and eccentrically mounted onto a second arbor to begin the second step of the manufacturing process. As an alternative, the part may be eccentrically mounted on the same arbor as used in the first step of the manufacturing process. FIGS. 11 and 12 show an embodiment of an arbor 200 for use in this second step of the manufacturing process. Conic section 140 having aspheric surface 150 and skirt 152 are eccentrically mounted onto arbor 200 for machining of the prism wedge portion of the prismatic intraocular lens. The part is then machined by a lathe to form the prism wedge and convex lens portion of the prismatic intraocular lens. To do this, the lathe cuts away a portion of conic section 140, leaving only a small cylindrical section around the center axis of the arbor. The resulting machined part is shown in FIGS. 13 and 14. As shown, after a portion of conic section 140 is removed, a small cylindrical section constituting prism wedge 44 and convex lens portion 42 having aspheric surface 60 are formed. The resulting part is then dismounted from the second arbor.

When mounting the part onto the arbor at the beginning of this second step of the manufacturing process, the displacement of the center of the part with respect to the center of the second arbor determines the magnitude of the desired prism wedge angle. For example, if the part were not eccentrically mounted, the lathe would leave a cylindrical section at the center of conic section 140. This center section would not be a prism, i.e. would have a prism wedge angle of zero. When mounting the part, as the distance from the center of the part to the center of the arbor is increased, the resulting prism wedge angle also increases.

As mentioned, the amount of displacement of the center of the part from the center of the arbor depends on the required prism wedge angle. To determine the amount of such displacement, a tangent line, shown as line 155 in FIG. 7, is made at points along surface 150 of conic section 140, such as tangent point B shown in FIG. 7. The angle between tangent line 155 and the x-y plane represents the prism wedge angle that would result if the part was eccentrically mounted so that tangent point B was a point on the base of the prism. Thus, when an appropriate tangent line is found to correspond to the required prism wedge angle, the part is eccentrically mounted so that the lathe cuts the prism with the tangent point at the base of the prism. The appropriate tangent line, tangent point, and amount of displacement of the center of the part from the center of the arbor can be determined by computer programs or other suitable methods.

In the third step of the manufacturing process, the machined part is mounted onto a third arbor. The arbor used in this third step has the same general configuration as the arbors used in the earlier steps of the manufacturing process. As an alternative, the part may be mounted on either of the arbors used in the first and second steps of the manufacturing process. The machined part, however, is mounted on its reverse side, the side having the convex lens portion and prism wedge, so that the flat skirt may be machined to form the haptics.

To form the haptics, the skirt is first machined to a desired thickness and then cut on a multi-axis precision mill. The mill is preferably controlled by commercially available software, such as CNC software sold by Servo Corporation. The resulting prismatic intraocular lens may be polished to form a finished device for implantation.

As an example of the manufacturing process, a PMMA blank of 22.489 mm in diameter and 6.5 mm thick was machined from a sheet of PMMA. The PMMA blank was mounted on an arbor. The blank was then machined by a lathe preprogrammed to cut aspheric surfaces according to Equation (2). The resulting part had a convex conic section having a diameter of 14.489 mm and a flat skirt having a width of 4.0 mm and a thickness of 0.25 mm. The power of the resulting lens was 20.0 diopters. The resulting machined part was then dismounted from the first arbor and eccentrically mounted onto a second arbor so that the center of the part was 4.489 mm from the center of the second arbor. A small cylindrical section of 5.0 mm diameter was machined by a lathe This cylindrical section constituted the lens portion and prism wedge of the intraocular lens. The resulting part was dismounted from the second arbor and mounted onto a third arbor. The flat side of the part was first machined on a lathe to a thickness of 0.18 mm. A mill was then used to form the haptics.

The image quality that results from an optical element, such as a prismatic intraocular lens, generally is assessed by measuring its modulation transfer function, a plot of image modulation versus spatial frequency of the target. Image modulation is a measurement of the contrast, or gray level difference, of an image. Image modulation is measured from 0 to 1, with 0 representing no contrast and 1 representing black/white contrast of an image. Spatial frequency is a measurement of image resolution and is given in terms of cycles per unit length. Generally, as spatial frequency lowers, image modulation increases.

Figure 8:
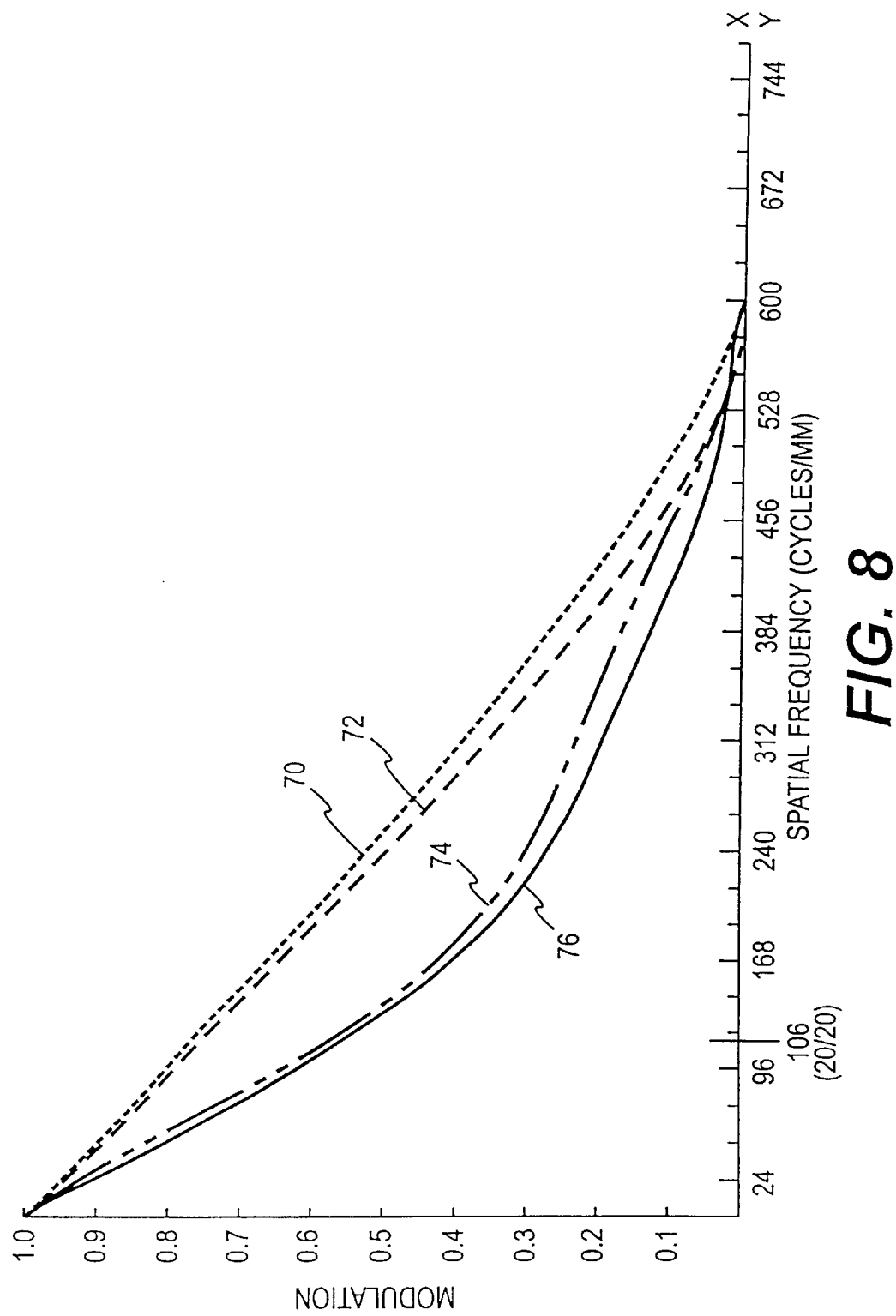
FIG. 8 is a modulation transfer plot comparing theoretically perfect image quality to image quality obtained by a prismatic intraocular lens according to the present invention.

FIG. 8 is a modulation transfer plot created by computer modeling an eye having a cornea aspherically corrected according to the Equation (2). The natural lens of the eye was replaced with a prismatic intraocular lens. The model eye used is the eye model adopted by the Optical Society of America (OSA) and is given in the OSA Handbook. In the model, corneal curvature is fixed at 43.0 D and the anterior chamber depth (the distance between the corneal surface and the anterior surface of the implant) is fixed at 3.8 mm. All combinations of values of c and k corresponding to prism wedge angles in the range of 15° to 40°, and implant powers in the range 15.0 D to 30.0 D were modeled. The axial length of the eye model (the distance between the anterior corneal surface and the retina) was also varied from 21.0 mm to 26.0 mm, in 1.0 mm increments. The retina was assumed to be flat in these model computations of the modulation transfer function. For purposes of the modeling, a refractive index of 1.492 for the prismatic lens was assumed.

The dashed plots labelled 70 and 72 indicate theoretically perfect modulation transfer plots for light rays of an object along the axis of the eye and for light rays of an object off the axis of the eye respectively. Visual acuity of 20/20 is equivalent to a spatial frequency of 106 cycles/mm.

The plots labelled 74 and 76 are the computer model results for the model eye incorporating a prismatic intraocular lens and a cornea aspherically corrected as described above. Plots 74 and 76 are for light rays of an object along the axis and off the axis of the eye respectively. Plots 74 and 76 indicate that a prismatic intraocular lens according to the present invention will deliver about 60% contrast (0.6 on the image modulation scale) at 20/20 acuity for black bars on a white background. The plots also indicate that a prismatic intraocular lens according to this invention will resolve features at significantly low contrast levels. For example, for gray bars on a gray background having a contrast only 20%, the resulting image contrast will still be higher than 10% (20%×60%) at 20/20 acuity. The lowest approximate image contrast that an eye can see is about 10%. Since most contrasts in the daily environment are about 20% to 90%, an implant with the modulation transfer function characteristic shown in FIG. 8 will decipher most contrasts and deliver comfortable vision at 20/20 acuity.

It will be apparent to those skilled in the art that various modifications and variations can be made in the inventive prismatic intraocular lens and related method of manufacture without departing from the scope or spirit of the invention. It is intended that the specification and examples be considered as exemplary only, with a true scope and spirit of the invention being indicated by the following claims.

What is claimed is:

1. A method for manufacturing an intraocular lens for restoring visual function to an eye, the intraocular lens including a convex lens optic for receiving and focusing light rays, a prismatic wedge adjacent to the convex lens optic for receiving and directing light rays to a functional portion of a retina of the eye, and means for fixing the lens optic and the prismatic wedge in the eye, the method comprising the steps of:

providing an optical blank;

forming a conic section having an aspheric surface and a flange portion from the optical blank;

forming the prismatic wedge and lens optic from the conic section; and forming the fixing means from the flange portion.

2. The method according to claim 1, wherein the conic section forming step includes the substep of forming the aspheric surface according to the formula:

$$Z(h)=ch^2/(1+\{1-(1+k)c^2h^2\}^{1/2})$$

where $Z(h)$=position of the aspheric surface on a z axis as a function of a radial distance h of the aspheric surface from the center of the optical blank, h=radial distance of the aspheric surface from the center of the optical blank, c=average aspheric curvature, and k=conic constant.

3. The method according to claim 1, wherein the fixing means is formed so that the convex lens optic is angularly oriented with respect to an optic axis of the eye when the intraocular lens is implanted in the eye.

4. The method according to claim 1, wherein the fixing means is formed so that the convex lens optic is posterior to the prismatic wedge when the intraocular lens is implanted in the eye.

5. The method according to claim 1, wherein the fixing means includes a pair of haptics.

6. The method according to claim 1, wherein the step of forming the fixing means includes machining the flange to a desired thickness.

7. The method according to claim 1, wherein the prismatic wedge and lens optic are formed by removing a portion of the conic section.

8. The method according to claim 1, wherein the step of forming the prismatic wedge and lens optic includes eccentrically mounting the conic section onto a fixture of a cutting device.

9. The method according to claim 8, wherein the conic section is eccentrically mounted according to a magnitude of a desired wedge angle of the prismatic wedge.

10. The method according to claim 8, wherein the step of forming the prismatic wedge and lens optic includes removing a portion of the conic section so that a cylindrical section remains about a center axis of the cutting device.

11. A method for manufacturing an intraocular lens for restoring visual function to an eye, the intraocular lens including a convex lens optic for receiving and focusing light rays, a prismatic wedge adjacent to the convex lens optic for receiving and directing light rays to a functional portion of a retina of the eye, and means for fixing the lens optic and the prismatic wedge in the eye, the method comprising the steps of:

providing an optical blank;

forming an aspheric surface from the optical blank;

forming the prismatic wedge and lens optic from the optical blank; and forming the fixing means from the optical blank.

12. The method according to claim 11, wherein the aspheric surface forming step includes forming the aspheric surface according to the formula:

$$Z(h)=ch^2/(1+\{1-(1+k)c^2h^2\})^{1/2})$$

where Z(h)=position of the aspheric surface on a z axis as a function of a radial distance h of the aspheric surface from the center of the optical blank, h=radial distance of the aspheric surface from the center of the optical blank, c=average aspheric curvature, and k=conic constant.

13. The method according to claim 11, wherein the prismatic wedge and lens optic are formed after the aspheric surface is formed.

14. The method according to claim 13, wherein the fixing means is formed so that the convex lens optic is angularly oriented with respect to an optic axis of the eye when the intraocular lens is implanted in the eye.

15. The method according to claim 13, wherein the fixing means is formed so that the convex lens optic is posterior to the prismatic wedge when the intraocular lens is implanted in the eye.

16. The method according to claim 13, wherein the fixing means includes a pair of haptics.

17. The method according to claim 13, wherein the step of forming the fixing means includes machining a flange portion of the optical blank to a desired thickness.

18. The method according to claim 13, wherein the step of forming the aspheric surface includes forming a conic section having the aspheric surface from the optical blank, and wherein the prismatic wedge and lens optic are formed by removing a portion of the conic section.

19. The method according to claim 18, wherein the step of forming the prismatic wedge and lens optic includes eccentrically mounting the conic section onto a fixture of a cutting device.

20. The method according to claim 19, wherein the conic section is eccentrically mounted according to a magnitude of a desired wedge angle of the prismatic wedge.

21. The method according to claim 19, wherein the step of forming the prismatic wedge and lens optic includes removing a portion of the conic section so that a cylindrical section remains about a center axis of the cutting device.

* * * * *